United States Patent [19]

Lowell

[11] Patent Number: 4,566,326
[45] Date of Patent: Jan. 28, 1986

[54] AUTOMATIC VOLUMETRIC SORPTION ANALYZER

[75] Inventor: Seymour Lowell, Albertson, N.Y.
[73] Assignee: Quantachrome Corporation, Syosset, N.Y.
[21] Appl. No.: 628,918
[22] Filed: Jul. 9, 1984
[51] Int. Cl.[4] ............................................. G01N 15/08
[52] U.S. Cl. .................................. 73/432 PS; 73/38
[58] Field of Search ............................. 73/432 PS, 38

[56] References Cited

U.S. PATENT DOCUMENTS

| | | | |
|---|---|---|---|
| 3,464,273 | 9/1969 | Hendrix | 73/432 PS |
| 3,500,675 | 3/1970 | Sandstede et al. | 73/432 PS X |
| 3,545,281 | 12/1970 | Johnston | 73/432 PS |
| 3,850,040 | 11/1974 | Orr, Jr. et al. | 73/432 PS |
| 3,915,636 | 10/1975 | Ford, Jr. et al. | 73/432 PS X |
| 3,943,754 | 3/1976 | Orr, Jr. | 73/432 PS X |
| 4,211,116 | 7/1980 | Pilat et al. | 73/432 PS X |
| 4,300,386 | 11/1981 | Gupta | 73/38 |
| 4,305,291 | 12/1981 | Nelson | 73/432 PS |
| 4,450,723 | 5/1984 | Scott | 73/432 PS |
| 4,489,593 | 12/1984 | Pieters et al. | 73/432 PS X |

FOREIGN PATENT DOCUMENTS

| | | | |
|---|---|---|---|
| 1057798 | 5/1959 | Fed. Rep. of Germany | 73/432 PS |
| 1202540 | 10/1965 | Fed. Rep. of Germany | 73/432 PS |
| 12423 | 1/1980 | Japan | 73/432 PS |

OTHER PUBLICATIONS

"Determination of Surface Area by Gas Chromatography"; *Analytical Chemistry*; vol. 33, No. 7, pp. 966-967; Jun. 1961; Ralph Stock.
"An Efficient Dynamic Method for Surface Area Determinations"; *Analytical Chemistry*; vol. 34, No. 9, pp. 1150-1155; Aug. 1962; H. W. Daeschner et al.
"A New Approach to Surface Area Determinations by Selective Gas Adsorption in a Nitrogen-Helium System"; (Paper #110 delivered at the Pittsburgh Conference on Analytical Chemistry and Applied Spectroscopy, Mar. 1-5, 1965); 16 pages; Jerome Kremen et al.
"Automatic Control of Pore Size Distribution Measurement in Solids"; *J. Sci. Instrum.*; vol. 44; pp. 922-925; Nov. 1967; D. G. Stevenson et al.

Primary Examiner—Stewart J. Levy
Assistant Examiner—Tom Noland
Attorney, Agent, or Firm—Hopgood, Calimafde, Kalil, Blaustein & Judlowe

[57] ABSTRACT

An automatic adsorption and desorption analyzer for independently performing analyses on a plurality of powder samples includes a manifold connected through a plurality of independently operated valves to a corresponding plurality of sample cells. A pressure transducer measures the manifold pressure and a plurality of pressure transducers are respectively coupled to the sample cells to independently measure the pressure at each of the sample cells. The system measures the volume of gas adsorbed (desorbed) by each of the samples that is required to establish specified equilibrium pressures at the sample cells, thereby to provide pressure-volume points which can be used to prepare adsorption (or desorption) isotherms, BET curves, and other information concerning the properties of the samples.

5 Claims, 7 Drawing Figures

AUTOMATIC VOLUMETRIC SORPTION ANALYZER

BACKGROUND OF THE INVENTION

The present invention relates generally to measurement techniques, and more particularly to an improved technique and apparatus for simultaneously and independently performing gas adsorption and desorption measurements on a plurality of different powder samples.

A great variety of applications in modern technology require accurate information concerning the microstructure of materials such as powders which are widely used, for example, as catalysts or in the production of paint, cement, and the like. This information includes the porosity and surface area of the powder material and the distribution of pore volume in the various sized pores.

One conventional manner of performing such measurements, which is disclosed, for example, in U.S. Pat. Nos. 3,211,006 and 3,555,912 involves the preparation of adsorption and desorption isotherms of the material in which equilibrium pressure is plotted against the volume of the gas (typically nitrogen) adsorbed or desorbed on the surface of the material. To prepare such isotherms the quantity of the gas adsorbed onto the solid surface or desorbed from the solid surface is measured at various specified pressures. The conventional gas adsorption process is, however, relatively slow, often requiring hours or sometimes even days to acquire the necessary data to accurately characterize the porosity and surface area of the material.

Such measurements are conventionally performed either manually or by the use of automated equipment on a single powder sample at a time. This results in either slow processing of the materials to make the necessary time-consuming measurements, the expenditure of a considerable amount of time and labor to operate several manual units, or the expenditure of large capital investments to purchase several automated units, so as to permit more than one more sample to be measured at a single time. The need has thus long existed for a unit that is capable of accurately and automatically analyzing the characteristics of a plurality of powder samples both rapidly and at a relatively low cost.

It is thus an object of the present invention to provide an analyzer unit capable of concurrently and independently obtaining data for a plurality of powder samples in a single measuring instrument.

It is a futher object of the invention to provide an analyzer unit of the type described which provides concurrent multiple measurements on powder samples both reliably and accurately and at a relatively low cost.

It is another object of the present invention to provide an analyzer unit of the type described in which the data derived for a plurality of samples can be stored and presented in any one of a number of different forms for each of the samples.

SUMMARY OF THE INVENTION

To these ends, the automatic measurement unit of the invention includes a common manifold in respective fluid communication through a plurality of isolation valves with a corresponding plurality of sample cells. A transducer is provided to measure the manifold pressure and a plurality of pressure transducers are respectively coupled to the sample cells to provide measurement of the respective pressures in the sample cells.

Operating automatically under the control of a microprocessor, which receives and processes information from the several pressure transducers and controls the operation of the isolation valves, the current cell pressure and manifold temperature are measured and the manifold pressure, which will when the manifold and cell are connected through the opened isolation valve, result in a pressure in the combined volume equal to a specified relative pressure, is calculated. The manifold is then pressured to the calculated value with nitrogen gas, and the cell isolation valve is opened to allow a volume of nitrogen to be admitted (or removed) into (or from) one of the sample cells which contain the solid adsorbent sample to be analyzed. As adsorption (or desorption) of the gas occurs in the sample, the pressure in the sample cell measured periodically by the cell pressure transducer varies until an equilibrium pressure is attained. The quantity of the gas adsorbed (or desorbed) at the equilibrium pressure is the difference between the amount of gas admitted (or removed) and the amount required to fill the space around the adsorbent (void space) which was previously determined.

This process is repeated for different volumes and relative pressures until a preselected number of data points have been produced for the sample. At one of several stages in the analysis sequence of a given sample cell at which an interval or delay is required, the processing or analysis is shifted for that period to another of the sample cells according to a priority sequence as determined by the microprocessor. This processing of shifting the operations between the sample cells on a priority basis continues in a sequence determined to achieve optimum analysis, until the required pressure-volume data points for all of the samples under analysis have been obtained.

BRIEF DESCRIPTION OF THE DRAWING

To the accomplishment of the aforementioned and to such further objects as may hereinafter appear, the present invention relates to a multi-sample material analyzer substantially as defined in the appended claims and as described in the followed specification as considered with the accompanying drawing in which:

DESCRIPTION OF THE PREFERRED EMBODIMENT

Figure 1:
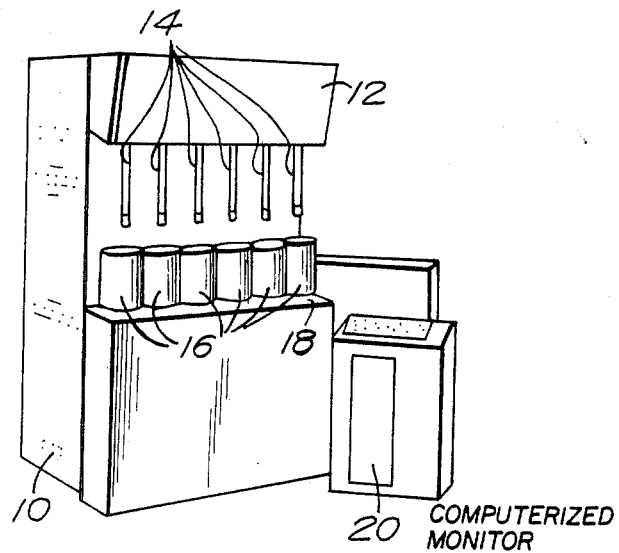
FIG. 1 is a perspective of a multi-sample material analyzer in accordance with an embodiment of the present invention.

The multi-sample surface analyzer of the invention, as shown in FIG. 1, is contained in a housing 10, which includes a manifold 12 from which a plurality (here six) of sample cell stations 14 extend downwardly. Positioned below the sample stations 14 are a corresponding number of Dewar flasks 16 supported on lower shelf 18. Positioned adjacent housing 10 is a computer and data terminal and monitor 20 which may also include a data printer-plotter (not shown).

Figure 2:
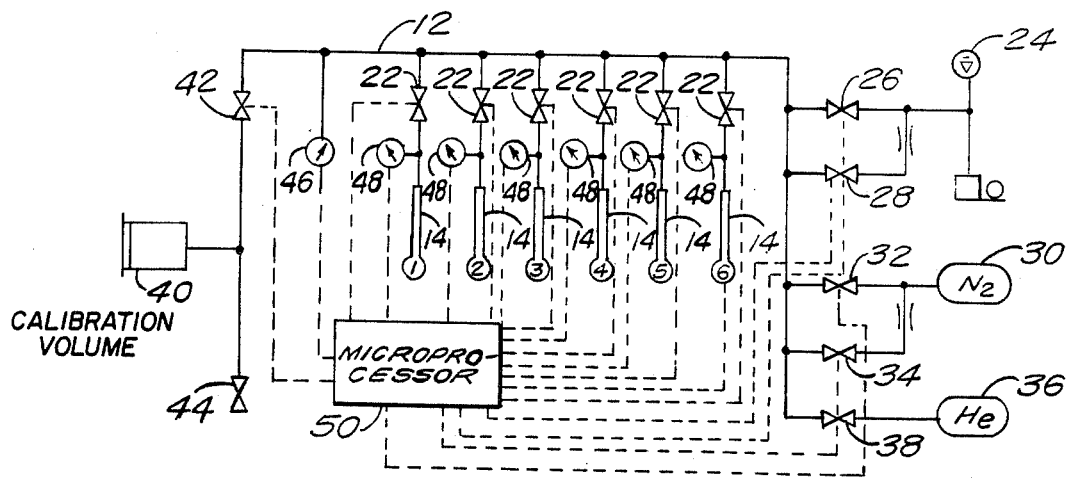
FIG. 2 is a schematic diagram of a portion of the analyzer of FIG. 1.

As described in greater detail below with respect to FIGS. 2 and 3, the analyzer unit of FIG. 1 is capable of performing concurrent and independent volumetric adsorption and desorption analyses on a plurality (here six) of solid powder samples placed within the sample cells 14. To this end, as shown in FIG. 2, the sample cells 14 are coupled to the manifold 12 by means of a plurality of isolation valves 22. Also coupled to the manifold 12 are a vacuum source 24 by means of valves 26, 28; a source of nitrogen 30 coupled through valves 32, 34; a source of helium 36 coupled through a valve 38; and a calibration volume 40 coupled through a valve 42. The manifold 12 may also be coupled to ambient by means of a manually controlled valve 44.

A manifold pressure transducer 46 is coupled to the manifold 12 to measure manifold pressure, and a plurality of sample cell pressure transducers 48 are respectively connected to each of the sample cells 14. A programmed microprocessor 50 is electrically connected (by means of the broken line connections in FIG. 2) to receive and transmit measurement and control signals from the transducers 46, 48 and to the valves 26, 28, 32, 34, 38 and 42.

In brief, the analyzer unit of the invention, as illustrated in FIGS. 1 and 2, operates under the control of microprocessor 50 in accordance with the program described below with respect to FIG. 3 to measure the quantity of gas adsorbed onto or desorbed from a solid surface of the sample material within the sample cells 14 at a preselected equilibrium pressure by the static volumetric method. The data is obtained by admitting or removing a known quantity of adsorbate gas (here nitrogen) from the manifold 12 into or out of the sample cell 14 containing the solid adsorbent maintained at a constant temperature below the critical temperature of the adsorbate. As adsorption or desorption occurs the pressure in the sample cell 14 changes until an equilibrium pressure is established. The quantity of gas adsorbed or desorbed at the equilibrium pressure is the difference between the amount of gas admitted or removed and the amount required to fill the space around the adsorbent (void space).

This volume-pressure data can be processed to produce at monitor 20, at the option of the unit operator the following well known outputs: a BET surface area plot, single-point BET area, a Langmuir surface area plot, adsorption and/or desorption isotherms, pore size and surface area distributions, micropore volume and surface area using t-plots, and total pore volume and average pore radius data. For additional information concerning the B.E.T. (Brunauer, Emmett and Teller, plot and the Langmuir surface area plot, see *Introduction to Powder Surface Area*, by Seymour Lowell, Wiley-Intersciece, 1979. Significantly, the analyzer unit of the invention is capable of performing such analyses substantially simultaneously and independently on a plurality (here six) of powder samples to produce this data in the manner now described with reference to the flow charts of FIGS. 3 and 4, which describe the processing sequence performed on the powder test samples.

Figure 3A:
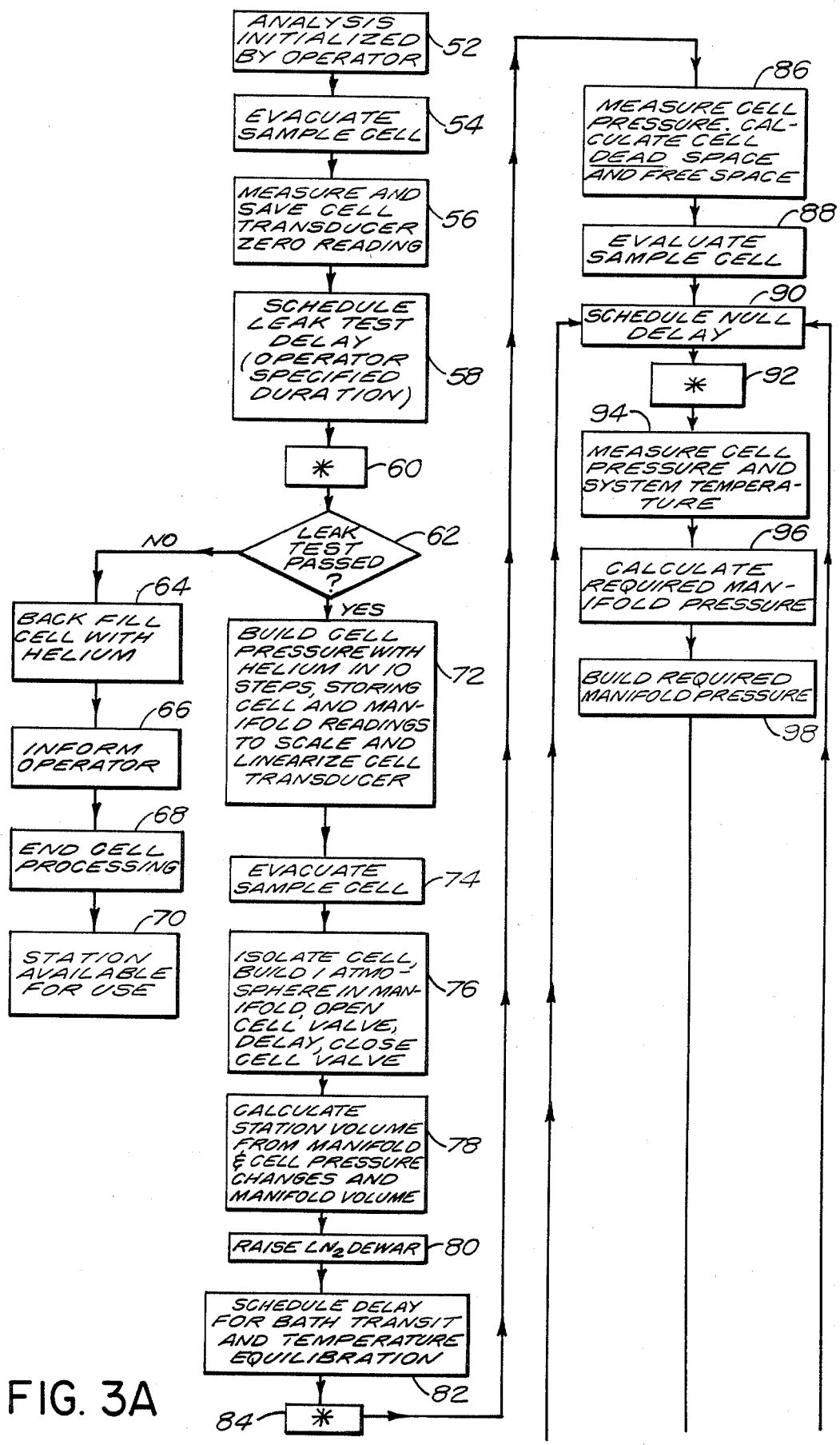
FIGS. 3A and 3B comprise a flow chart of a portion of the program implemented in the microprocessor of the analyzer of the invention.
Figure 3B:
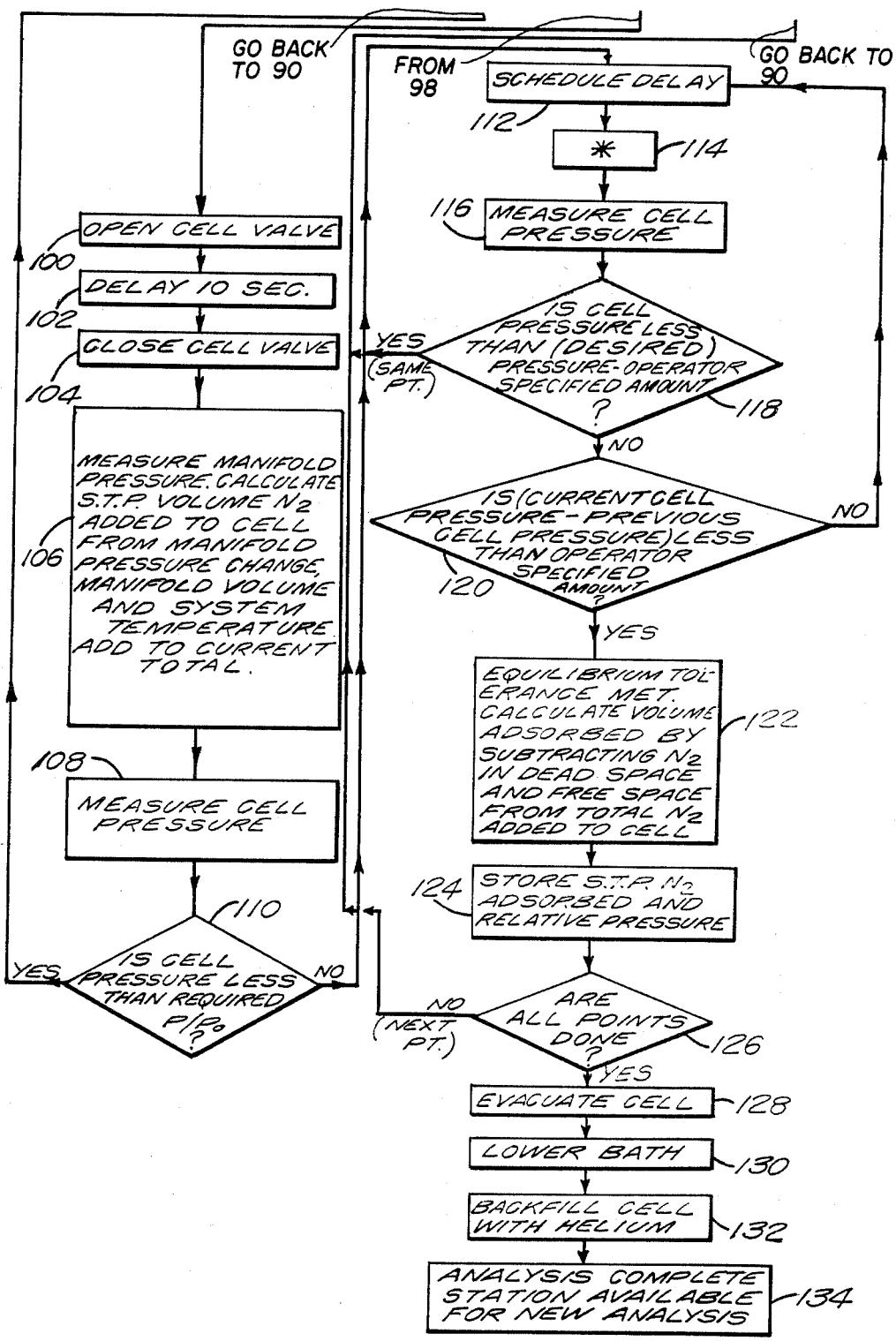

FIG. 3 describes in flow-chart form the steps carried out in analyzing a sample in one of the plurality of sample cells. It will be understood that although processing is actually performed on only one sample at any instant of time, at certain intervals in each sample processing sequence, indicated by an asterisk in the flow chart, processing of all or part of a measurement sequence can also be performed on one or more additional samples. Accordingly, during a given interval all or part of a sample analysis can be carried out on as many as six of the samples contained in the sample cells 14 in the analyzer unit of FIG. 2.

Returning to FIG. 3, before an analysis is begun on any sample, a leak test is performed to assure that there are no leaks in the system that would cause an error in the measurement on the sample. To this end, after the analysis is initiated by the operator at step 52, the particular sample cell 14 is evacuated at step 54 by opening its associated valve 22 to the manifold 12, and the vacuum valves 26, 28. Thereafter, at step 56, the zero reading of the pressure transducer 48 associated with that sample cell is measured and stored.

The duration of the leak test period (typically 1–30 minutes) is scheduled by the operator at step 58 during which the cell transducer pressure reading is monitored to determine if any leakage occurs in the cell. During this test interval, as indicated by the asterisk at step 60, a measurement procedure on another sample cell or station can be processed. Such intervals occur at other times during a measurement sequence on a sample, as indicated by the asterisks at other scheduled intervals in the sequence, as will be apparent from the following discussion of a measurement sequence.

Thus, if at the end of the leak test delay implemented at step 58, it is determined at step 62 that the sample cell has not passed the leak test, that is, there is a leak in the system somewhere in the sample cell or in the piping between that cell and the manifold, the cell is backfilled with helium at step 64 and the operator is informed that a leak has been detected at step 66. At this point, processing at that cell is terminated at step 68, and an indication is provided at step 70 that the station is now available for use to make measurements on a sample.

If the determination made at step 62 is that the cell has passed the leak test, the pressure in the cell at step 72 is increased by adding a quantity of helium (a gas that is not adsorbed by the solid material in the cell) to the cell at, say, 10 increments by opening the valve 22 between the sample cell 14 and manifold 12. The cell and manifold pressures at pressure transducers 48 and 46, respectively are stored and compared so that the less precise cell transducer 48 is linearized or correlated with the more precise manifold pressure transducer 46, thereby to achieve greater accuracy in the pressure measurements that follow.

Thereafter, as shown at step 74, the cell is evacuated of the helium gas, and, as shown at step 76, the cell isolation valve 22 is closed to isolate the cell from the manifold and a pressure of, say, 1 atmosphere of helium is built up in the manifold 12. Thereafter, the valve 22 is opened and after a delay is closed. In the next step 78, the overall volume of the sample cell station is calculated from the measured changes in the valves of the manifold and sample cell pressures and the known volume of the manifold. The calculated station volume is stored in the microprocessor and then at step 80, the Dewar flask 16 beneath the sample cell under study and which contains liquid nitrogen is raised so that the sample and a portion of the sample cell are immersed in the liquid nitrogen. The volume of the cell under the liquid nitrogen and at a low temperature of about 77.4° K. is designated as the dead space, whereas the remaining volume of the sample cell and the piping between it and the manifold, which are at ambient temperature, is designated as the free space. The aforementioned station volume calculated in step 78 is the sum of the free space and the dead space.

Thereafter, at step 82, a delay is scheduled to allow the sample in the liquid nitrogen bath to reach an equilibrium temperature. During this interval at the asterisked step 84, as at step 62, processing can be performed on any other of the samples in the unit along the same sequence as described here. Following this interval, the processing is resumed at step 86 at which point in the process the sample cell pressure is measured at the cell pressure transducer, and, in addition, from the difference in the measured manifold pressure before and after the control valve 22 to the sample cell is closed, the cell dead space and free space are calculated and their values stored in the microprocessor.

Thereafter, at step 88, the sample cell is once again evacuated and at step 90 a null delay is scheduled to allow the cell to be fully evacuated. In this interval, as indicated at the asterisked step 92, processing can again be carried out on another powder sample. Following this null delay period, the sample cell pressure and system temperature are measured at steps 94, and at step 96 the required manifold pressure is calculated from the ideal gas equation of state. This calculated manifold pressure is the pressure that will result in a cell pressure that is greater by an amount preselected by the system operator than a desired value of P/Po that is attained when the manifold and cell are later connected by the opening of the cell valve 22 in order to allow for some adsorption of gas by the sample.

Thereafter, at step 98, the manifold pressure is built up to the value calculated in step 96, and at step 100, the cell valve 22 is opened. After a delay of say 10 seconds established at step 102, the cell valve 22 is closed at step 104. Following the closure of the cell valve, the manifold pressure is again measured from the change in the manifold pressure before and after the cell valve was opened to allow nitrogen gas to flow from the manifold to the cell. The volume of nitrogen (STP) gas added (or dosed) into the sample cell can be calculated from the standard ideal gas equation of state. That computed volume is added to any volume that had been previously computed during the processing sequence. This calculated and stored volume thus represents the total volume of nitrogen gas introduced into the sample cell from the manifold.

Thereafter, at step 108, the cell pressure is measured, and at step 110 a determination is made as to whether the measured cell pressure is less than the desired or requested value of P/Po, wherein P is the measured pressure and Po is the saturated vapor pressure of nitrogen. If the measured cell pressure is less than this desired value, the sequence is returned to step 90 and additional nitrogen is introduced or dosed into the sample cell until a determination is made at step 110 that the cell pressure is equal to or exceeds the desired value of P/Po.

When the measured cell pressure is at the desired value, a delay is scheduled at step 112 and during this interval, at asterisked step 114, processing of other samples in other cells can be carried out. Thereafter, at step 116, the cell pressure is measured again, and a determination is made at step 118 as to whether as a result of the additional adsorption of nitrogen by the sample, the measured cell pressure is less than the desired pressure less a specified amount preset by the operator.

If the determination made at step 118 is in the affirmative, the sequence is returned to step 90 to cause additional gas to be introduced into the sample cell in order to achieve the desired pressure. If the determination made at step 118 is negative, the determination is then made at step 120 as to whether the differences between the current measured cell pressure and the previously measured cell pressure is less than a specified amount previously established by the operator. If this determination is negative, indicating that an equilibrium cell pressure has not yet been reached, the process sequence returns to step 112 and continues to repeat steps 112 through 120 until an equilibrium cell pressure is reached, as indicated by an affirmative determination at step 120.

When this occurs, at step 122, the pressure equilibrium tolerance has been satisfied and the volume of nitrogen that has been adsorbed by the sample at this time is calculated by subtracting the volume of nitrogen in dead space and free space, calculated from the measured pressure and temperature, from the total volume of nitrogen added to the cell, as computed in step 106.

Figure 5:
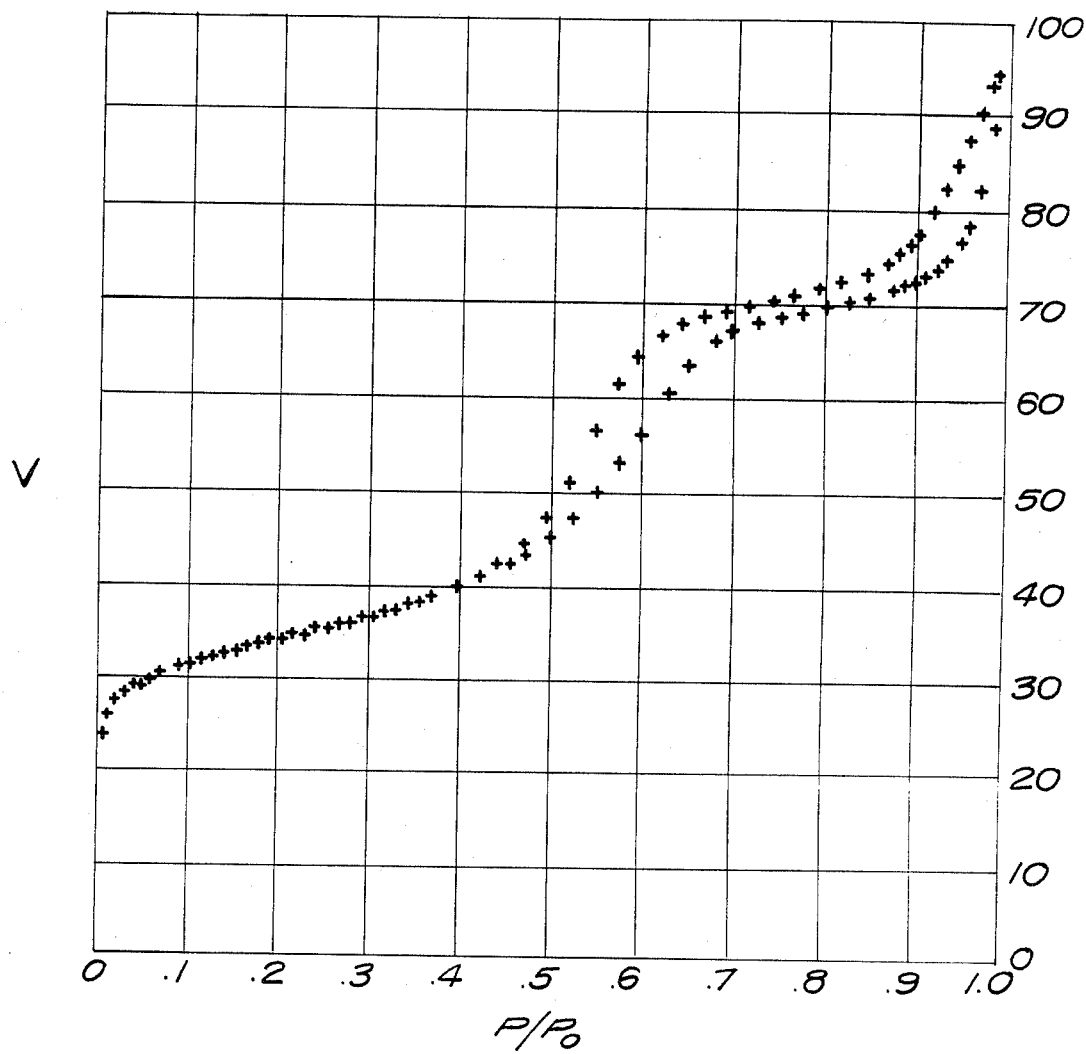
FIG. 5 is a typical adsorption-desorption isotherm that can be produced from the data obtained by the analyzer of the invention.

The thus derived values of the volume of adsorbed nitrogen and relative pressure are stored at step 124 to establish one point on the adsorption isotherm (FIG. 5), and a determination is then made at step 126 as to whether all desired data points on the isotherm have been thus determined. If not, the process is return to step 90 to process the sample cell at a higher manifold pressure to determine the next isotherm point. If all data points on the isotherm have been obtained, the cell is evacuated at step 128, the Dewar flask 16 is lowered away from the sample cell at step 130, and the cell is backfilled with helium at step 132. At this time, the adsorption sequence analysis is complete for the sample and the station is now available for a new sample analysis as indicated at step 134.

It will be appreciated that the flow chart of FIG. 3 illustrates the computation of an adsorption sequence. To perform a desorption sequence, essentially the same sequence of steps is followed with the nitrogen in the case of desorption being removed rather than introduced into the sample cell, and the relative pressures being measured on a decreasing rather than an increasing scale. That is, when data is measured on the desorption isotherm the required relative pressure P/Po is initially set near unity, wherein the derivation of adsorption data, the analysis beginning with the sample under vacuum, or a relative pressure P/Po of near zero.

As noted, the steps in the flow chart of FIG. 3 which contain an asterisk, namely steps 60, 84, 92 and 114, are points at which processing on one sample or station is suspended while one or more other sample cell stations connected to the common manifold can be processed. As noted in FIG. 3, that interval is scheduled at various points in the process, and is resumed once the delay interval is completed. The null delay at step 90 only causes processing to switch to another station if the time for processing to resume at that station is already passed. In this manner, a check on pressure equilibrium at any sample is assigned a higher priority than other steps in the process sequence then underway at the other samples.

Figure 4:
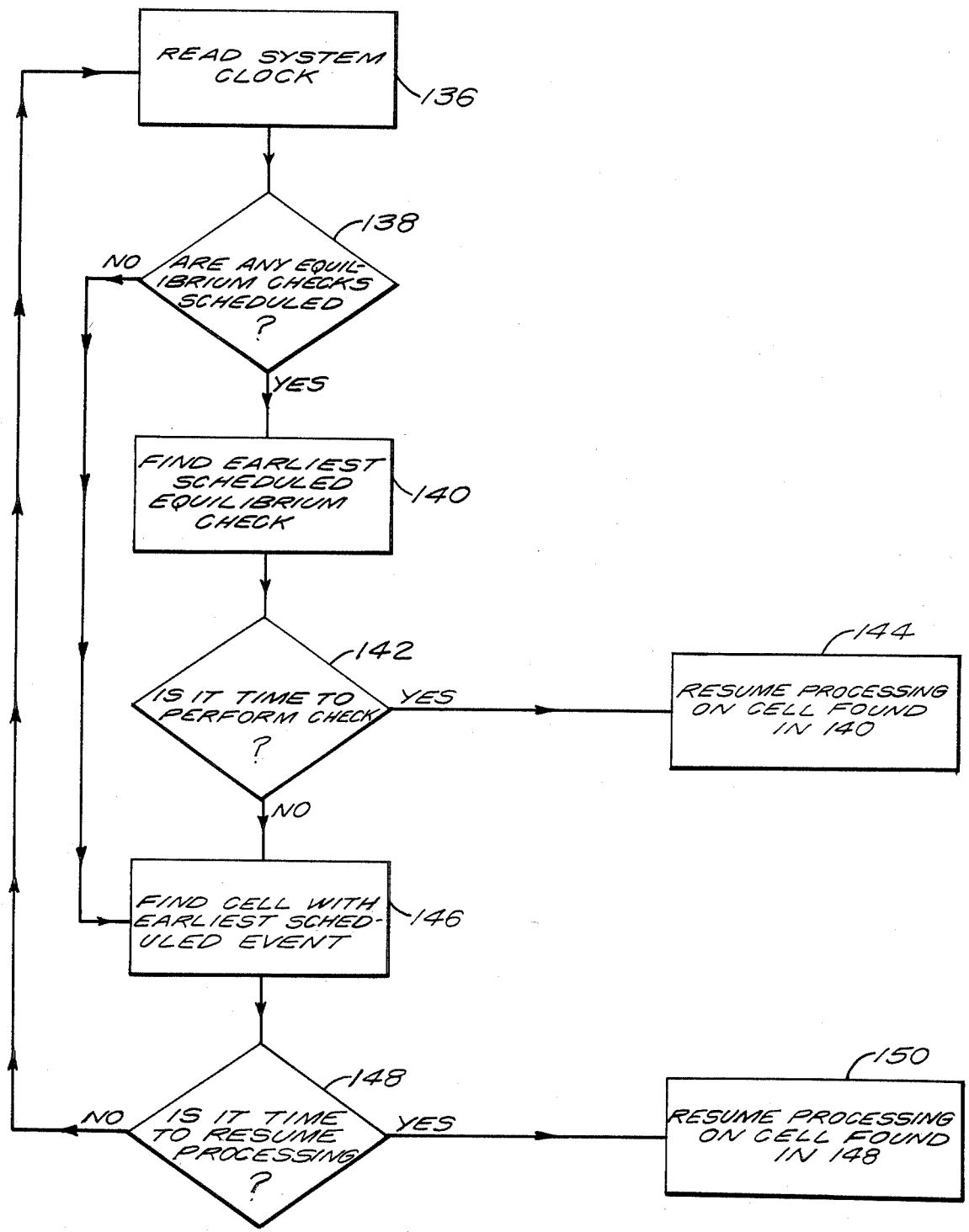
FIG. 4 is a flow chart of another portion of the program implemented in the microprocessor.

The control of the sequence of the processing among the various stations is achieved by the sequencing routine performed in accordance with the flow chart of FIG. 4, which is carried out for all sample cell stations whenever the sample then undergoing processing arrives at an interval as indicated by the asterisk in the flow chart of FIG. 3.

As shown in the flow chart of FIG. 4, at step 136 the system clock is read, and at step 138 a determination is made as to whether any equilibrium checks in any of the sample cell stations are then scheduled. If an equilibrium check is scheduled at that time at one of the sample cells, at step 140, the sample cell at which the earliest scheduled equilibrium check is identified or located. Thereafter, at step 142, the determination is made if it is time to perform an equilibrium check at that sample cell station by comparing the scheduled time with the current system time as determined at step 136.

If it is determined at step 142 that it is time to perform an equilibrium check at the station sample cell identified at step 140, then at step 144, processing is resumed at the cell identified at step 140. In the event that the determination made at either step 138 or step 142 is a negative, then at step 146 the cell with the earliest scheduled event other than an equilibrium check is identified or located, and at step 148 the determination is made as to whether it is time to resume processing at the cell identified in step 146. If the determination made at step 148 is in the affirmative, processing on the cell selected in step 146 is resumed as indicated at step 150. If the determination at step 148 is in the negative, the routine is returned to initial step 136 and then repeats until processing is resumed at one of the cells.

Thus, although in the system of the invention only one sample cell may be processed at a given single instant of time, whenever a delay interval occurs in that processing sequence, another processing sequence may be initiated or resumed at any of the sample cell stations which is at the highest level of priority for processing, as determined by the routine illustrated in the flow chart of FIG. 4.

Figure 6:
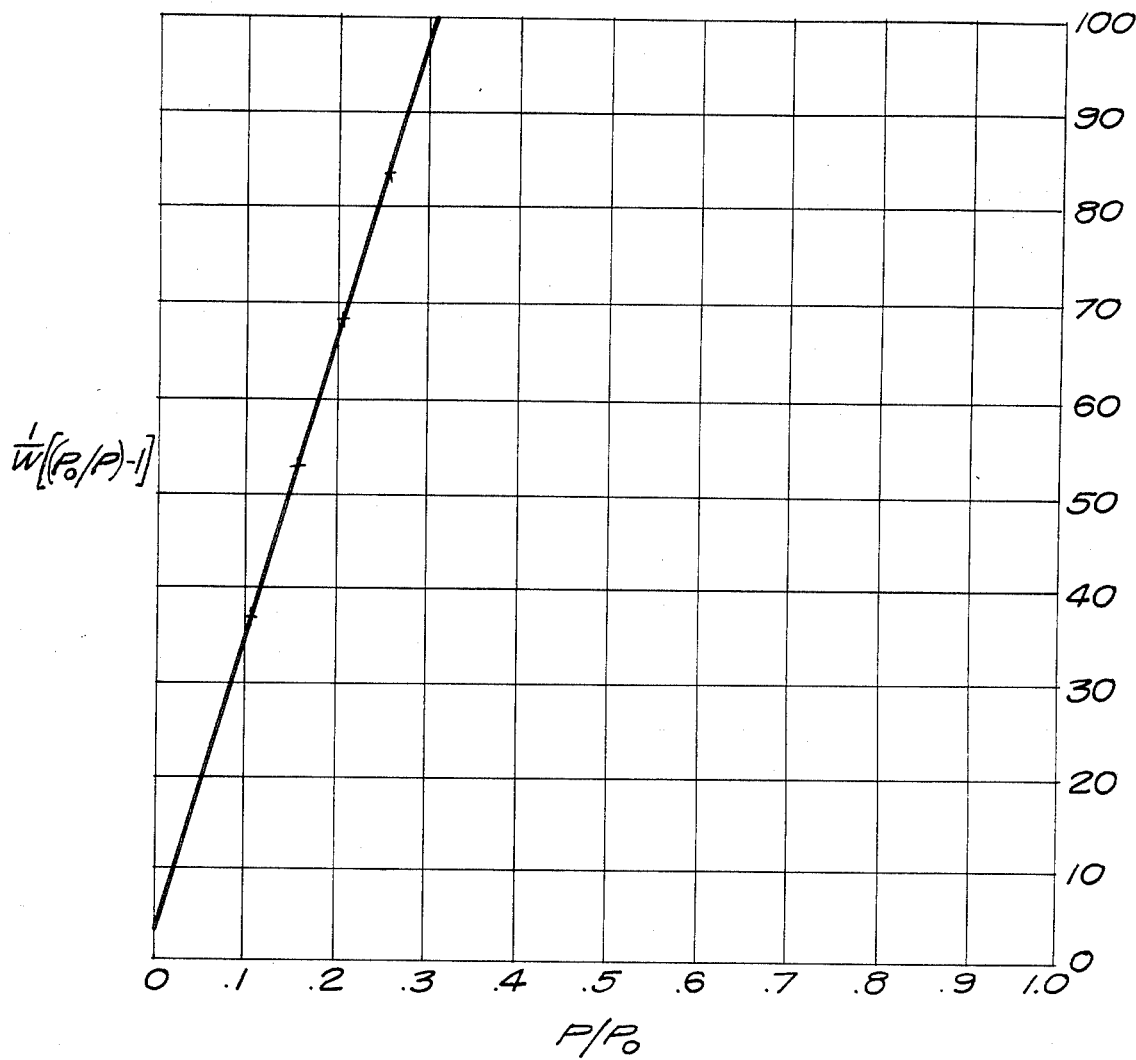
FIG. 6 is a typical B.E.T. curve that can be produced from the data obtained by the analyzer of the invention.

As described hereinabove with respect to the flow chart of FIG. 3, the analyzer unit of the invention develops for each sample cell a series of values of adsorption or desorption volumes at a series of preset equilibrium pressures. Those data points are fed to the computer 20 which, under the selection of the operator, can produce plots or printouts or displays of the data in any one of a number of different useful forms including a complete adsorption-desorption isotherm, of the type shown in FIG. 5, or a BET plot of the type shown in FIG. 6, the meaning of the symbols therein being the obvious one's, and which can be used to determine the surface area of the sample in a per se known manner. For a further explanation of the axes of the plots of FIGS. 5 and 6, see *Introduction to Powder Surface Area*, by Seymour Lowell, Wiley-Interscience, 1979.

Other data plots and printouts that can be produced from the pressure-volume data points obtained for one or more of the test samples processed include Langmuir plot, mesopore volume and surface area distributions, micropore volume and surface area, total pore volume, and average pore radius. The processing of the raw data and the production of the printouts and plots for the sample in one of the sample cells may be carried out while processing continues on samples in the other cells or the one for which data is being processed.

It will be appreciated from the foregoing description of the invention that such data and printouts that characterize the sample material in the cell can be concurrently and independently obtained for a plurality of such samples, here shown, for purposes of example, as being six in number. It will thus also be appreciated that modifications may be made to the embodiment of the invention hereinabove described, such as increasing or decreasing the number of sample cell stations, without departing from the spirit and scope of the invention.

What is claimed is:

1. An analyzer for performing independent measurement analyses on a plurality of powder samples, said analyzer comprising a common manifold, a plurality of sample cells for holding a powder sample to be analyzed, a plurality of valve means respectively interposed between said manifold and said plurality of sample cells, control means operatively connected to said plurality of valve means for selectively effecting fluid communication between said manifold and said plurality of sample cells, a first pressure sensor in communication with said manifold, and a plurality of additional second pressure sensors in respective communication with said plurality of sample cells for respectively determining the pressure in said sample cells, said control means being effective to close a selected one of said valve means while pressure equilibrium is being established in an associated one of said sample cells and to open selectively others of said valve means to allow gas to be transferred from said manifold to associated others of said sample cells.

2. The analyzer of claim 1, in which said control means is operatively coupled to said first pressure sensor and to said plurality of second pressure sensors and said analyzer further comprises means for measuring the volume of gas adsorbed or desorbed by the powder sample in each sample cell in establishing a predetermined pressure therein.

3. The analyzer of claim 2, in which said control means comprises means for selecting one of said sample cells for sample analysis on a priority basis over the others of said plurality of sample cells.

4. In a process for analyzing a plurality of different powder samples in a sample analyzer comprising the steps of selectively coupling a common manifold to one of a plurality of sample cells each of which contains a powder sample, measuring the pressure in the manifold, determining the volume of gas admitted to or removed from said selected one of said sample cells in establishing a predetermined equilibrium pressure thereat, shutting-off the transfer of gas from said manifold to said one sample cell while pressure equilibrium is being established therein while allowing the transfer of gas from said manifold to selected others of said sample cells, and repeating the aforementioned steps for individual others of said sample cells, thereby to establish a plurality of volume-pressure points for characterizing the sample in each of said sample cells.

5. The process of claim 4, further comprising the steps of interrupting the analysis being performed at the selected one of said sample cells at a predetermined interval during an analysis sequence, and, during said interval, performing at least a portion of an analysis on another of said sample cells.

* * * * *